United States Patent [19]

Koblish et al.

[11] Patent Number: 5,779,646
[45] Date of Patent: Jul. 14, 1998

[54] DEFLECTABLE BIOPSY CATHETER

[75] Inventors: Josef V. Koblish, Framingham; Thomas T. Coen, Westboro, both of Mass.; George J. Klein, London, Canada

[73] Assignee: E.P. Technologies Inc., San Jose, Calif.

[21] Appl. No.: 918,913

[22] Filed: Aug. 27, 1997

Related U.S. Application Data

[63] Continuation of Ser. No. 395,968, Feb. 28, 1995, Pat. No. 5,715,832.

[51] Int. Cl.$^6$ .................................................... A61B 5/00
[52] U.S. Cl. ........................................................ 600/567
[58] Field of Search ........................... 600/562, 564–567; 606/167, 170

[56] References Cited

U.S. PATENT DOCUMENTS

| | | |
|---|---|---|
| 3,342,175 | 9/1967 | Bulloch . |
| 3,964,468 | 6/1976 | Schulz . |
| 4,184,486 | 1/1980 | Papa . |
| 4,649,924 | 3/1987 | Taccardi . |
| 4,953,559 | 9/1990 | Salerno . |
| 4,960,134 | 10/1990 | Webster . |
| 5,083,565 | 1/1992 | Parins . |
| 5,122,137 | 6/1992 | Lennox . |
| 5,133,727 | 7/1992 | Bales et al. . |
| 5,217,458 | 6/1993 | Parins . |
| 5,228,451 | 7/1993 | Bales et al. . |
| 5,281,218 | 1/1994 | Imran . |
| 5,287,857 | 2/1994 | Mann . |
| 5,354,297 | 10/1994 | Avitall . |
| 5,383,874 | 1/1995 | Jackson et al. . |
| 5,386,818 | 2/1995 | Schneebaum . |
| 5,482,054 | 1/1996 | Slater et al. . |

FOREIGN PATENT DOCUMENTS

| | | |
|---|---|---|
| 0 317 526 A1 | 5/1989 | European Pat. Off. . |
| WO 94/07446 | 4/1994 | WIPO . |
| WO 94/22384 | 10/1994 | WIPO . |

*Primary Examiner*—Max Hindenburg
*Attorney, Agent, or Firm*—Oppenheimer Wolff & Donnelly LLP

[57] ABSTRACT

A deflectable biopsy catheter for obtaining a tissue sample from a body cavity of a patient comprising: an axially elongated catheter shaft having proximal and distal portions respectively terminating at proximal and distal ends, the catheter shaft being sized and constructed to be advanced into a body cavity of a patient; a deflection wire coupled to the distal portion of the catheter shaft and extending within the catheter to the proximal end thereof; and a pair of biopsy jaws coupled to the distal end of the catheter shaft and having first and second opposed free cutting surfaces exposable for contact with a selected area of tissue within the patient's body cavity and movable with respect to each other to cut a tissue sample from the selected area of tissue. Schemes for obtaining samples from body cavities (e.g., the gastrointestinal tract, the heart, the intestines, the uterus, the muscles, the bile duct, and the esophagus) are disclosed. Schemes for treating tissue by ablation or by electro-coagulation are also disclosed.

41 Claims, 8 Drawing Sheets

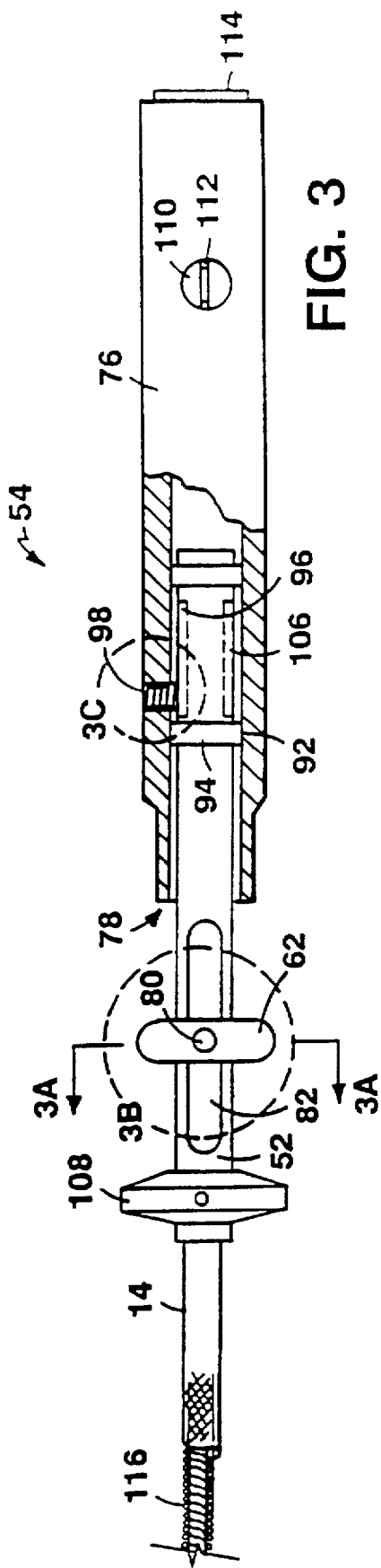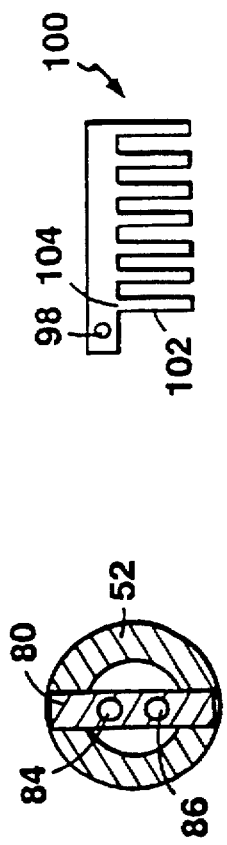

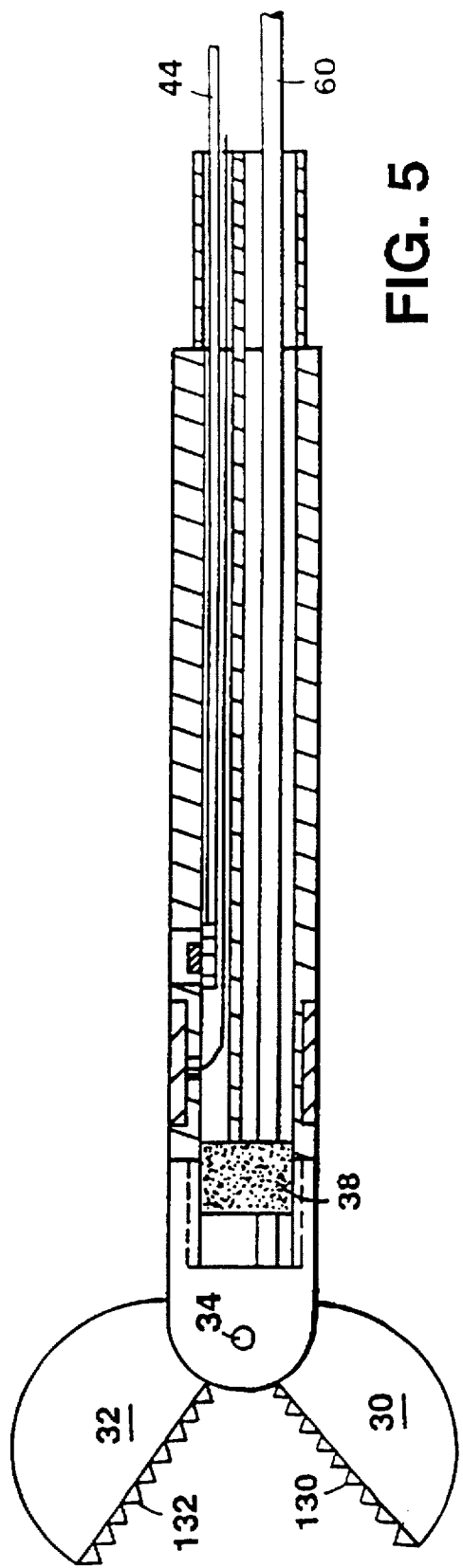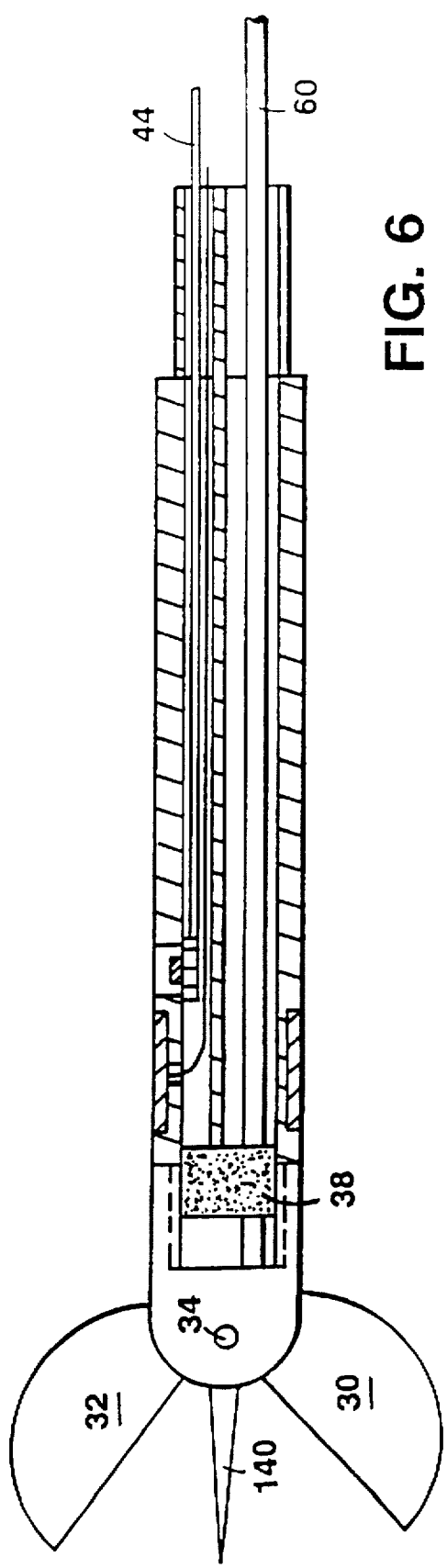

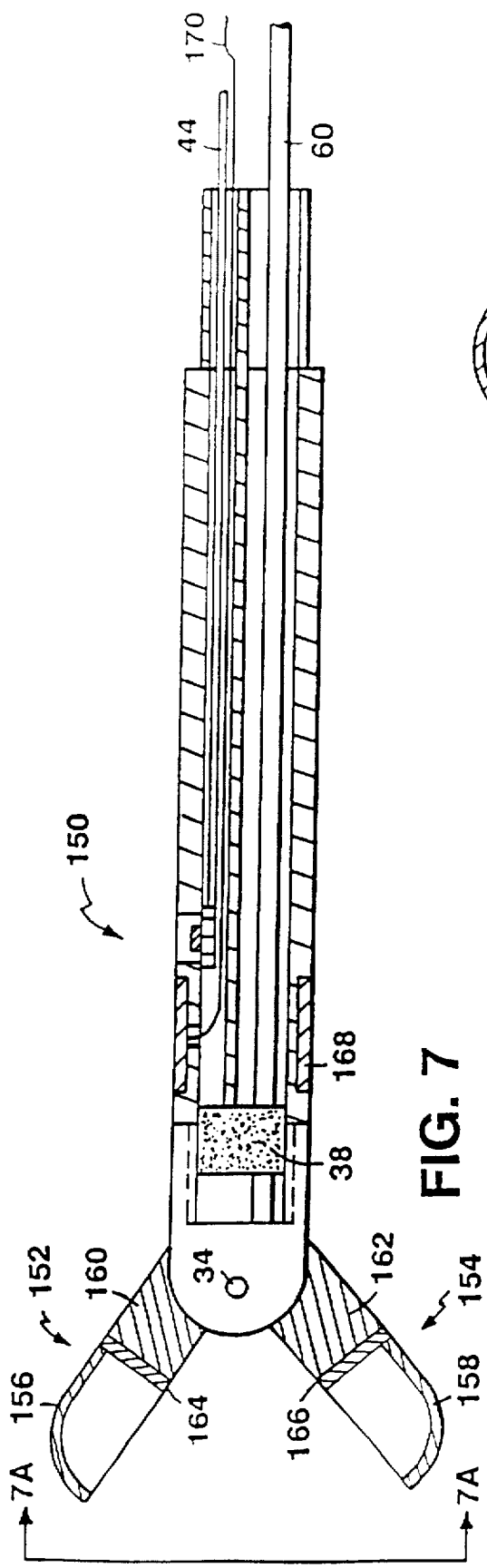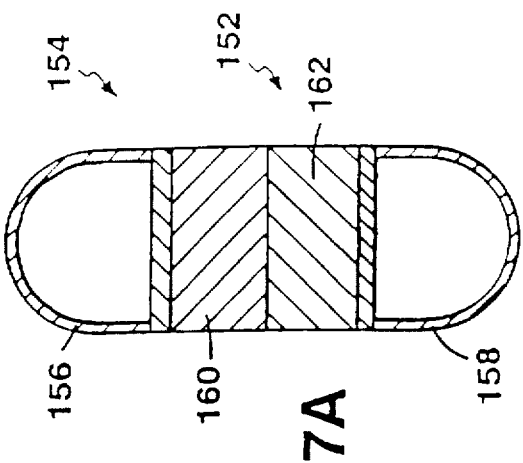
FIG. 7
FIG. 7A

DEFLECTABLE BIOPSY CATHETER

This application is a continuation of U.S. application Ser. No. 08/395,968, filed Feb. 28, 1995 now U.S. Pat. No. 5,715,832.

BACKGROUND

This invention relates to a deflectable biopsy catheter.

Biopsy is a commonly performed surgical procedure in which tissue samples are obtained for diagnostic purposes. Such a procedure requires cutting a tissue sample and then retrieving the cut sample. In this application, sampling forceps are typically carried on the distal end of a catheter and positioned around a tissue portion selected for removal and diagnosis. The sampling forceps cut the selected tissue and retain the sample so that it is removed from the patient's body along with the catheter.

SUMMARY

In a first aspect, the invention features a deflectable biopsy catheter for obtaining a tissue sample from a body cavity of a patient comprising: an axially elongated catheter shaft having proximal and distal portions respectively terminating at proximal and distal ends, the catheter shaft being sized and constructed to be advanced into a body cavity of a patient; a deflection wire coupled to the distal portion of the catheter shaft and extending within the catheter to the proximal end thereof; and a pair of biopsy jaws coupled to the distal end of the catheter shaft and having first and second opposed free cutting surfaces exposable for contact with a selected area of tissue within the patient's body cavity and movable with respect to each other to cut a tissue sample from the selected area of tissue.

Embodiments may include one or more of the following features. The biopsy jaws are preferably formed of hollow cup-shaped members that are pivotally hinged together about a pivot bearing coupled to the distal end of the catheter shaft. An axially elongated actuation wire is preferably coupled to the biopsy jaws and extending proximally therefrom to the proximal end of the catheter shaft, the actuation wire being constructed and arranged to selectively move the jaws. A tracking member is preferably coupled to the deflection wire and is preferably constructed and arranged to track movement of the actuation wire and to couple tension on the actuation wire to the deflection wire to counteract force applied by the actuation wire to the distal portion of the catheter during movement of the jaws. The deflection wire and the actuation wire are preferably arranged on radially opposed sides of the catheter axis in the distal portion of the catheter shaft. The distal portion of the catheter shaft preferably defines first and second non-coaxial lumens: the first and second lumens being radially offset from the axis of the catheter shaft and the deflection wire being disposed in the first radially offset lumen and the actuation wire being positioned in the second radially offset lumen. The opposed jaws are preferably formed from electrically conducting material and together form a generally dome-shaped outer electrically conducting surface.

In some embodiments, the cutting surfaces of the biopsy jaws preferably comprise a plurality of serrated teeth for cutting body tissue. Some embodiments include a needle coupled to the distal end of the catheter shaft and constructed and arranged to penetrate heart tissue to a selected depth. Embodiments suited for use in the heart include biopsy jaws that respectively include hollow cup-shaped distal sections for cutting tissue coupled to solid proximal sections having flat surfaces exposable for contact with tissue for ablation. The cup-shaped portions are preferably electrically insulated from the ablation electrode sections.

In another aspect, the invention features a scheme for obtaining a tissue sample from a body cavity of a patient comprising the steps of: advancing a deflectable biopsy catheter, as defined above, within a body cavity of a patient; steering the catheter through the patient's body cavity and to a selected portion of body tissue by selectively deflecting the distal end of the catheter by applying tension to the deflection wire; opening the opposed jaws in the vicinity of the selected portion of body tissue; torquing the catheter shaft and deflecting the distal end of the catheter so that the opposed jaws are positioned about the selected portion of body tissue; and closing the jaws to cut a sample of tissue from the selected portion of body tissue.

In some embodiments, the opposed biopsy jaws together form an exposed electrically conductive surface and the selected area of heart tissue is electro-coagulated by supplying to the electrically conductive surface formed by the biopsy jaws energy sufficient to achieve tissue electro-coagulation. The distal portion of the catheter is preferably deflected to increase pressure applied by the exposed conductive surface of the biopsy jaws against the selected portion of tissue during electro-coagulation.

In another aspect, the invention feature a scheme for obtaining a tissue sample from the heart of a patient comprising the steps of: advancing a deflectable biopsy catheter, as defined above, through the vasculature of a patient, wherein the opposed biopsy jaws together form an exposed electrically conductive electrode surface and further comprising a second electrically conductive electrode surface; steering the catheter through the vasculature and into the heart of the patient by deflecting the distal end of the catheter by applying tension to the deflection wire; selecting the area of heart tissue to be diagnosed based on measurements of electrical potentials within the patient's heart between the first and second electrode surfaces; opening the opposed jaws in the vicinity a selected portion of heart tissue; torquing the catheter shaft and deflecting the distal end of the catheter so that the opposed jaws are positioned about the selected portion of heart tissue; and closing the jaws to cut a sample of tissue from the selected portion of heart tissue.

In some embodiments, the area of heart tissue to be ablated is selected based on measurements of electrical potentials within the heart between the first and second electrode surfaces. In some cases the area of heart tissue selected to be ablated is ablated by supplying to the electrically conductive surface formed by the biopsy jaws energy sufficient to achieve tissue ablation.

Embodiments may include one or more of the following advantages. The ability to deflect the catheter enables an operator to precisely position the biopsy jaws within a body cavity of a patient (e.g., around interfering anatomical body features). The catheter allows an operator to close the biopsy jaws onto a tissue sample without displacing the position of the catheter tip. This increases the reliability of the procedure and decreases the overall procedure time, increasing safety and patient comfort. In addition, by deflecting the distal tip of the catheter, the pressure of the biopsy jaws against the tissue to be cut is increased, improving the ability to take samples and improving the uniformity and the effectiveness of tissue electro-coagulation. The catheter achieves high torque transmission without sacrificing flexibility of the catheter shaft, so that the catheter may easily follow the inherent tortuosity of a patient's anatomy without risk of injury to the patient. This permits an operator to precisely control the position of the catheter tip during advancement of the catheter through the body. The deflectability and steerability of the catheter enable the biopsy catheter to be advanced within a patient's body with or without the assistance of an endoscope or the like. The multi-modality features of the catheter suited for use in the heart enhances an operator's ability to treat and diagnose the condition of a patient's heart.

Other features and advantages of the invention will become apparent from the following.

DESCRIPTION

FIG. 1A is a cross sectional view of the body of the catheter shown in FIG. 1 taken along the line 1A—1A.

FIG. 1B is an enlarged side view, in partial cross section, of the distal tip of the catheter of FIG. 1.

FIG. 1C is a cross sectional view of the catheter tip shown in FIG. 1B taken along the line 1C—1C.

FIG. 1D is a diagrammatic front view of the distal end of the catheter shown in FIG. 1B with the jaws fully open.

FIG. 3 is a diagrammatic side view, in partial cross section, of the proximal end portion of the catheter of FIG. 1.

FIG. 3A is a cross sectional view of the proximal end of the catheter shown in FIG. 3 taken along the line 3A—3A.

FIG. 3C is a diagrammatic top view of a lock mechanism in the proximal end of the catheter shown in FIG. 3.

FIG. 5 is a diagrammatic side view, in partial cross section, of the distal end of an alternative deflectable biopsy catheter.

FIG. 6 is a diagrammatic side view, in partial cross section, of the distal end of an alternative deflectable biopsy catheter.

FIG. 7 is a diagrammatic cross-sectional side view of a deflectable biopsy ablation catheter.

FIG. 7A is a diagrammatic end view of the catheter of FIG. 7.

STRUCTURE

Figure 1:
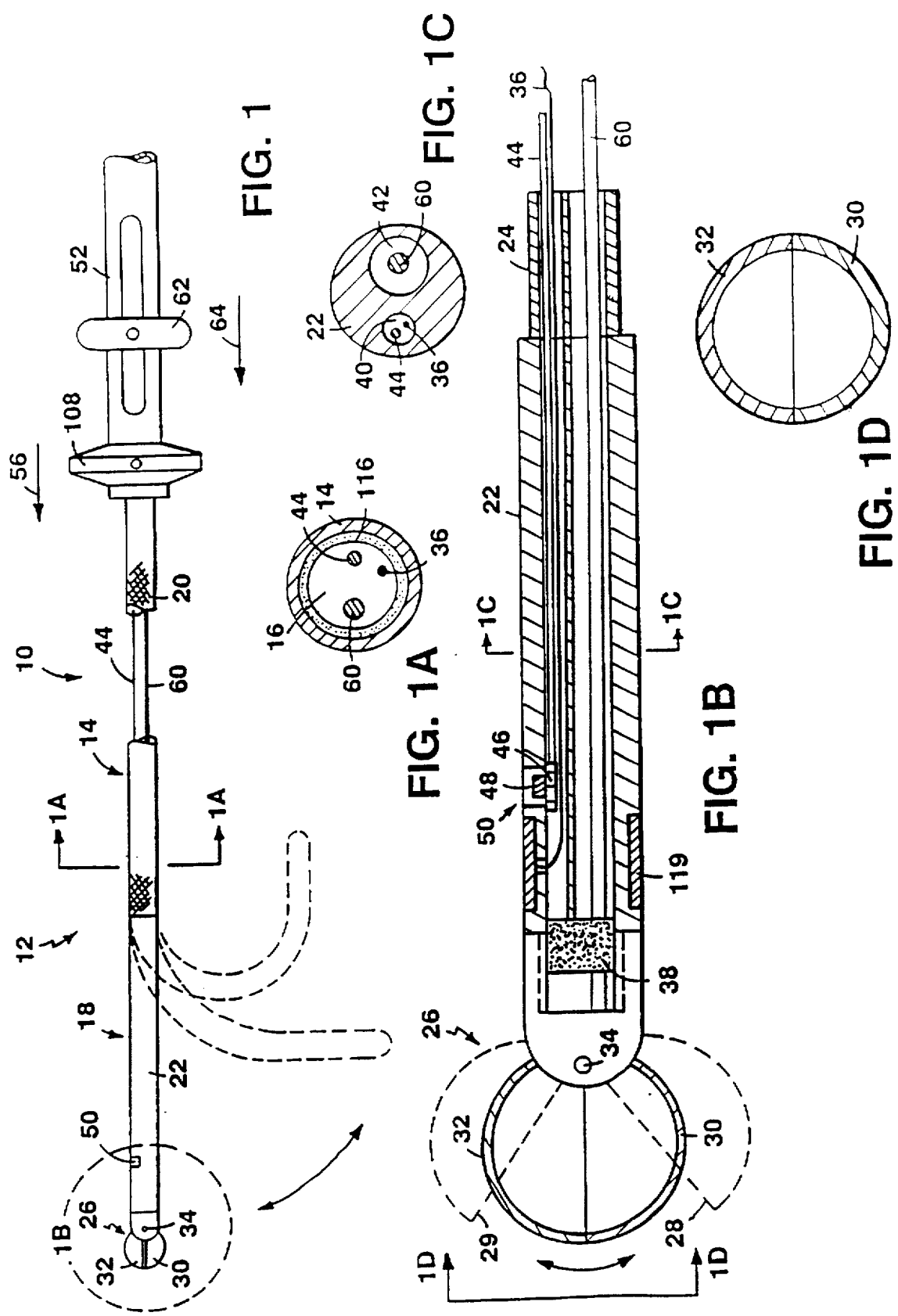
FIG. 1 is a diagrammatic side view of a deflectable biopsy catheter.

Referring generally to FIGS. 1–1D, a deflectable biopsy catheter 10 includes an elongated catheter shaft 12 that has a relatively stiff hollow catheter body 14 that defines a lumen 16 and is bonded to a relatively flexible, deflectable distal tip 18. The catheter body includes a braided shaft 20. The distal tip of the catheter is formed from a short section of flexible tubing 22 that is preferably more flexible than the catheter body. The proximal end of the distal tip of the catheter includes a circumferential notch 24 (FIG. 1B) that has an outer diameter selected to snugly fit within the distal lumen of catheter body 14. The catheter tip is bonded to the catheter body using a conventional adhesive.

As shown in greater detail in FIG. 1B, catheter 10 further has a biopsy sampler 26 that is mounted on catheter tip 18. Biopsy sampler 26 is formed from two opposed jaws 30, 32 that are hinged together and movable with respect to each other, about a pivot bearing 34, into a closed position (shown by solid lines) and into an open position (shown by dashed lines). The jaws are formed into hollow hemispherical or cup-shaped members that have respective circumferential free cutting edges 28, 29 that cooperate with each other to cut tissue when the jaws are closed. The jaws, when closed, together form a dome-shaped outer surface that is exposed for contact with body tissue and that may be constructed for electro-coagulation. A rubber seal 38 prevents the seepage of blood and other body fluids into the catheter through the distal end of the device.

Distal tube 22 defines a pair of non-coaxial lumens 40, 42. A deflection wire 44 extends into lumen 40 to a position near the distal end of the catheter where it is crimped onto a stainless steel hypotube 46 which is welded to a short length (e.g., 0.2 inches) of stainless steel ribbon 48 to form a "T" structure. The ribbon sits within an opening 50 in the wall of the catheter tip. The ribbon is larger than opening 50. The ribbon is bonded to the catheter tip by filling the opening with a biocompatible adhesive. Deflection wire 44 is coupled from the catheter tip to a piston 52 which is slidably disposed within a bore of a control handle 54. The catheter tip is deflected by gripping the control handle housing and moving the piston distally (shown by arrow 56) out of the piston chamber, which tenses the deflection wire and draws the distal end of the catheter proximally toward the handle. Because the deflection wire is attached to one side of the catheter tip, the tip preferentially bends radially in the direction of attachment (shown in phantom in FIG. 1).

The deflection wire is preferably surrounded by a teflon sheath that extends from a location near the proximal end of the piston chamber to a distal location that is spaced proximally of the distal end of the deflection wire by at least a distance equal to the maximum operating length of longitudinal movement of the piston relative to the housing (e.g., ½ to ¾ inch). The sheath provides lubricity for the movement of the deflection wire, and also serves to maintain the deflection wire in generally coaxial relation with the catheter body 14. The deflection wire is maintained in coaxial relation with the catheter body so that the length of the deflection wire and the on-axis length of the catheter body are substantially the same, whether the catheter body extends around a curve or not. In this arrangement, less energy is required for rotation of the catheter tip. This allows the tip to be more responsive to rotation of the handle and therefore more easily controlled.

As shown in FIG. 1, an actuation wire 60 is coupled between the jaws and an actuation knob 62 at the proximal end of the catheter. The jaws are opened when the actuation knob is moved in the distal direction (shown by arrow 64), and the jaws are closed when the actuation knob is move in the opposite direction. The diameter and the constituent material of the actuation wire are selected so that the actuation wire has sufficient axial stiffness to support the axial load necessary to open the jaws. In a presently preferred embodiment, the actuation wire is formed from conductive material (e.g., nitinol) and serves to deliver rf electro-coagulation energy to the jaws.

Figure 2:
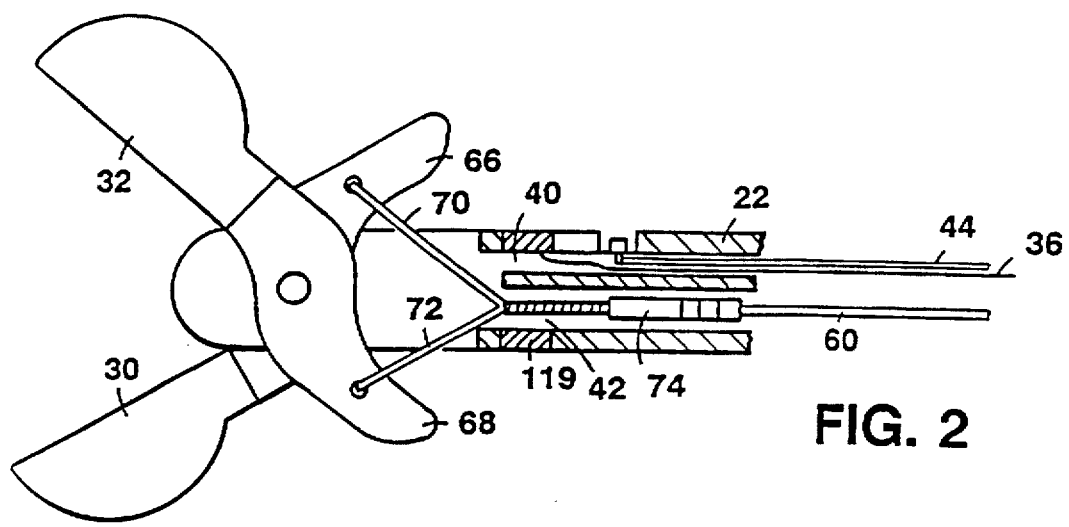
FIG. 2 is a diagrammatic cross-sectional side view of the distal tip of the catheter of FIG. 1.

As shown in FIG. 2. in a presently preferred embodiment, jaws 30, 32 include respective proximal extensions 66, 68 onto which are looped respective wire strands 70, 72. The length of strand 70 is made longer than the length of strand 72, as shown. Strands 70, 72 are wound together and are coupled to actuation wire 60 by a crimp junction 74. Actuation wire 60 and deflection wire 44 are respectively disposed in the non-coaxial lumens 40, 42 so that when the jaws are closed, proximally-directed tension, applied by actuation wire 60 to the catheter tip (urging displacement of the position of the catheter tip), is substantially counteracted by application of proximally-directed tension to deflection wire 44, as described below in connection with FIG. 3B. The radial position of the actuation wire relative to the central axis of the catheter tip is adjusted to achieve the desired compensation effect (e.g., by changing the radial position and the size of lumen 42).

Referring to FIG. 3, control handle 54 includes a cylindrical housing 76 that has a cylindrical bore 78. Piston 52 has a distal end that is attached to the proximal end of the catheter shaft and a proximal end that is slidably disposed within the bore of housing 76. The proximal end of catheter body 14 fits within a bore defined by piston 52 and abuts against a lip region of the piston where the diameter of the piston bore is reduced. The catheter body is attached at the proximal end to the piston using, e.g., a cyanoacrylate adhesive.

Figure 3B:
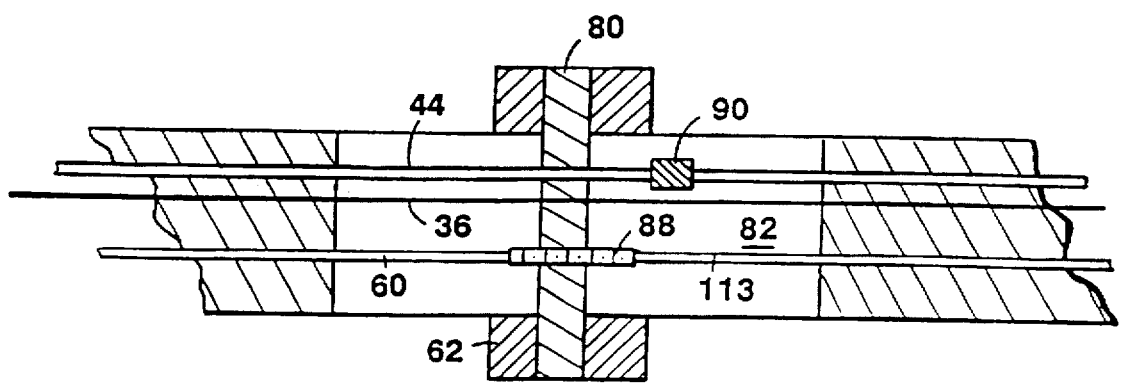
FIG. 3B is a cross sectional side view of the proximal end of the catheter shown in FIG. 3.

As shown in FIGS. 3A and 3B, actuation knob 62 is mounted onto a slide bar 80 which freely slides within a slot 82 in piston 52. Slot 82 has a hole 84 through which deflection wire 44 passes and a hole 86 at which the proximal end of the actuation wire is attached, e.g., by a solder crimp joint 88. A tracking device 90 (e.g., a stop) is attached to deflection wire 44 so that when the actuation knob is moved in the proximal direction to close the jaws, the stopper is engaged by slide bar 80, which exerts tension on the deflection wire to compensate for the forces applied by the actuation wire that act to displace the position of the catheter tip. Thus, the tracking member tracks movement of the actuation wire and couples tension applied to the actuation wire to the deflection wire for counteracting force applied by the actuation wire to the distal portion of the catheter.

Referring back to FIG. 3, the handle housing is generally symmetrical about its longitudinal axis, allowing the handle to be freely rotated by an operator. The piston includes a circumferential O-ring notch 92 that carries an O-ring 94 to provide a watertight seal between the piston and the wall of the piston chamber. The piston includes a first slot 96 that extends along a portion of its length proximal of the o-ring notch. A set screw 98 extends from the wall of the housing into the slot. Slot 96 includes a keyway lock profile 100 (FIG. 3C). The set screw restricts the longitudinal movement of the piston by engaging the walls 102 of the keyway lock profile. To steer the catheter tip, the piston is pushed in and out of the slots 104, defined by the walls of lock profile 100, until a desired tip deflection is achieved. An annular thumbrest 108 is then twisted to lock the piston in place relative to the control handle housing.

A second slot 106 is disposed on the opposite side of the piston as the first slot. Within the second slot are two adjacent, short (e.g., ⅛ inch long) pieces of teflon tubing that provide a lubricous surface to facilitate axial movement of the piston with respect to the handle housing. The distal end of the piston extends beyond the distal end of the housing so that it may be manually controlled by a user. Annular thumbrest 108 is attached to the distal end of the piston to facilitate axial movement of the piston.

Deflection wire 44 extends through the axial bore of the piston, through hole 84 in slide bar 80 to the proximal end of handle housing 76, where it is attached by an anchor 110. The anchor extends into a transverse hole in the portion of the housing between the connector and the piston chambers. The anchor is rotatable within the hole, but fits snugly so that it does not rotate freely. The anchor includes a transversely extending hole that may be rotated into alignment with the axis of the handle housing to receive the proximal end of the deflection wire. The anchor is rotated by means of a flat screw driver slot 112 to adjust the tension on the deflection wire.

Actuation wire 60 extends from the catheter body proximally through the axial bore of the piston to the proximal end of the control handle housing. A lead wire 113 is coupled to the actuation wire at the actuation knob to provide electrical energy to the actuation wire. At the proximal end of the handle housing the lead wire is bowed slightly to provide slack as the catheter is manipulated. The lead wire is connected to a plug 114 that extends proximally from the handle housing.

A closely wound spring coil 116 is disposed within the lumen of the catheter shaft. The coil extends distally from the proximal end of catheter body 14 to near the distal end of the catheter body. The coil structure efficiently transmits torque from the proximal end of the catheter to the catheter tip because the direction of the applied torque substantially corresponds to the incompressible axis of the coiled wire. In a presently preferred embodiment, the proximal end of the coil is securely attached to the proximal end of the catheter body, but the distal end of the coil is unattached to the catheter body. This allows a certain amount of stretch in the portion of the coils on the outside portion of a bent region of the catheter body, thereby achieving a high flexibility while providing the efficient torque-transmitting capability of the coil. In other words, as the catheter body is bent e.g., through the aortic arch, the upper part of the coil opens up to maintain the flexibility, but the inner portion of the coil is tight in compression. In this position, the coil, together with the catheter body, are able to transmit torsional and tensile forces exerted on the proximal end of the catheter. Further details regarding the arrangement of the coil and the catheter shaft are provided in U.S. Ser. No. 08/138,863, filed Oct. 19, 1993, which is herein incorporated by reference.

In a presently preferred embodiment, the jaws are made of stainless steel and are each roughly 4 mm in diameter (e.g., for electrophysiological procedures). The ring electrode is made of platinum and is about 1.3 mm wide. The actuation wire is made of nitinol and has a diameter of about 0.018–0.019 inch. The deflection wire is made of nitinol and has a diameter of about 0.01 inch. Typically a force of about 10–12 pounds is required to deflect the distal portion of the catheter by one hundred and eighty degrees. Preferably, the handle and piston are formed from acetal (e.g., DELRIN™). For cardiac sampling procedures, the length of the catheter shaft is about 48 inches (120 cm), while the length of the catheter tip is typically between 1½ and 3 inches (3.8–7.6 cm); the outer diameter of the catheter body is typically about 7 French (0.23 cm), and the outer diameter of the catheter tip is typically about 6 French (0.2 cm). The choice of the catheter dimensions, e.g., for other applications, will depend upon the anatomy of the patient and the type of procedure to be performed. The braided shaft is formed from counter-wound double stainless steel wires with a pick count (i.e., the number of times that wires cross a unit of tube length) of about thirty-two to thirty-four times per inch that are braided over a polyurethane tube which is over-extruded with a polyurethane coating that bonds through the braid to the inner tubing to form a unitary structure with a hardness of about D70. The distal portion of the catheter shaft is formed from a polyurethane extrusion and preferably has a hardness of about D60. The spring coil 72 has an inside diameter of about 0.038 inch (0.10 cm) and an outside diameter of about 0.058 inch (0.15 cm), and fits closely within the inside diameter of the shaft 30, which is about 0.059–0.062 inch (0.15–0.16 cm). The coil is made from e.g., #302 stainless steel wire that has a circular cross-section (although a wire with a rectangular cross-section may be used). The coil may be fabricated from other spring-like materials, such as nitinol.

During fabrication of catheter 10, catheter body 14 slides over a tip assembly that includes catheter tip 18 with the biopsy jaws, and the deflection and actuation wires. All of the wires are pulled through the catheter body. The spring coil slips over the proximal end of the deflection and actuation wire and into the catheter body. The proximal end of the catheter body is then attached to the distal end of the piston portion of the control handle.

OPERATION

Figure 4:
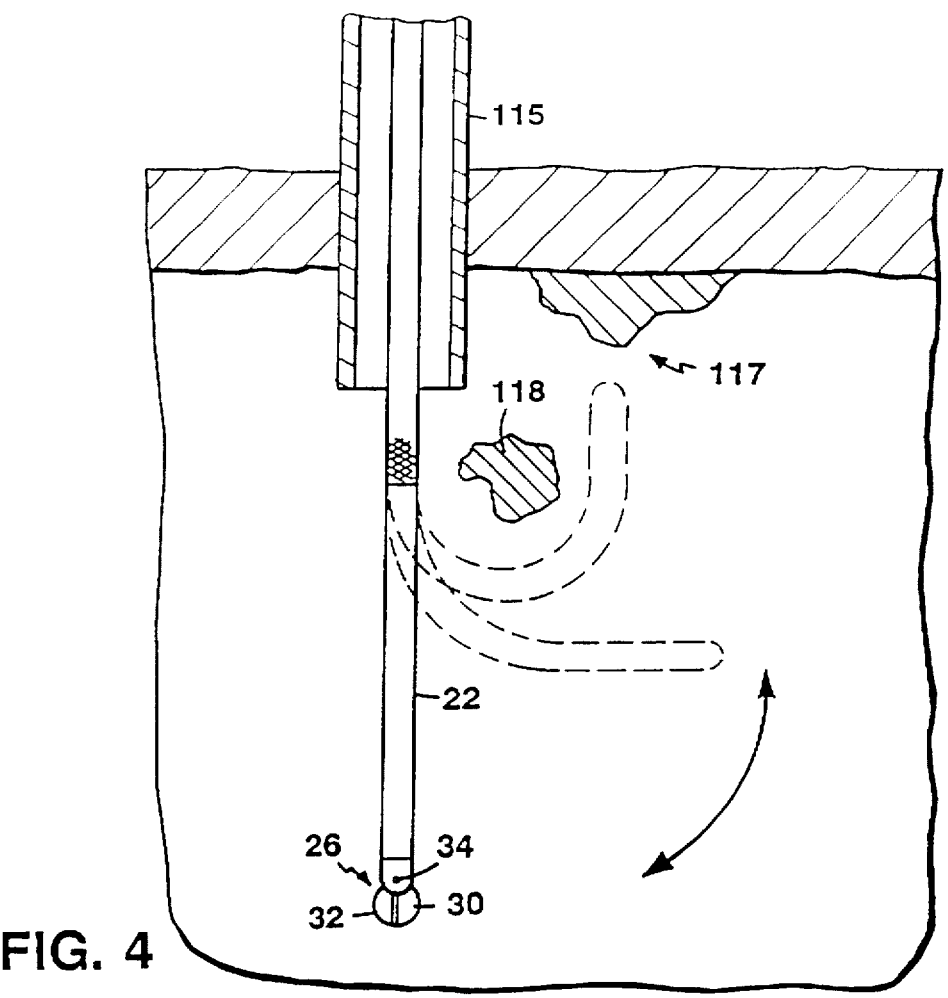
FIGS. 4 and 4A are diagrammatic side views of the catheter of FIG. 1 disposed within a body cavity of a patient for obtaining a tissue sample.

Referring to FIG. 4, deflectable biopsy catheter 10, pushed through a working channel (typically having an inner diameter of about 2.8–4 mm) of an endoscope 115, enters a cavity within a patient's body (e.g., the gastrointestinal tract, the intestines, the uterus, the muscles, the bile duct, the heart, and the esophagus) to a location 117 identified as a potential abnormal tissue site. By torquing the catheter body and deflecting the catheter tip under fluoroscopic visualization, the catheter is steered around interfering anatomical features 118 within the body cavity to the abnormal site. During advancement of the catheter, the position of the endoscope is held steady to serve as a reference platform. We note that the deflectability and the steerability of catheter 10 allows an operator to advance the catheter within a patient's body without the assistance of an endoscope or the like.

Figure 4A:
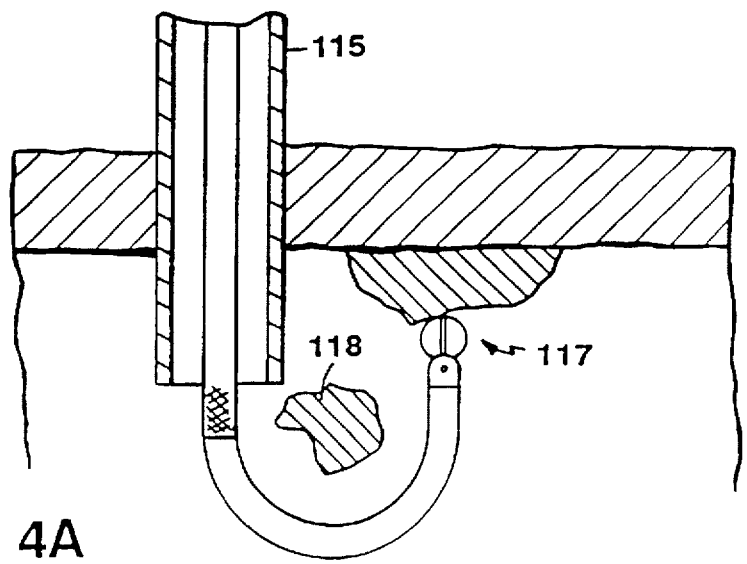

Referring to FIG. 4A, upon achieving proper placement, the operator opens the jaws about the sampling site 117 by pressing forward on the actuation knob of the catheter. With the jaws fully open, the catheter tip is deflected by pushing distally on thumbrest 108 (indicated by arrow 56 in FIG. 1), which presses the jaws against the myocardial tissue, increasing the normal force 121 applied by the electro-coagulation surfaces of the jaws. The deflection of the catheter tip is locked in place by twisting the piston relative to the handle housing. The operator then moves the actuation knob in the proximal direction to close the jaws about the selected portion of tissue and to cut the tissue. The cut tissue is retained within the cavity defined by the jaws during removal of the catheter from the patient's body.

In some cases it may be necessary to prevent the sampled region of tissue from bleeding. In these cases, rf energy is delivered to the exposed, dome-shaped, electrically conductive outer surface formed by the jaws to electrically coagulate the tissue in the sampled region. For improved electro-coagulation, the catheter tip is deflected so that the dome-shaped electrode surface is pressed into the tissue in the sampled region. This increases the depth and the uniformity of electro-coagulation.

Other embodiments are within the scope of the claims.

Referring to FIG. 5, in an alternative embodiment, instead of flat surfaces, the exposable cutting surfaces of jaws 30, 32 include respective arrays of serrated teeth 130, 132 that mate together when the jaws are closed. Teeth 130, 132 provide additional cutting and tearing force for obtaining tissue samples.

Alternatively, as shown in FIG. 6, an axially oriented needle 140 is mounted on the distal end of the catheter. Needle 140 is constructed to penetrate tissue to a selected depth (e.g., 1–3 mm) beyond the proximal end of the jaws to facilitate fixation of the distal end of the catheter against body tissue, increasing the stability of the device and increasing the accuracy of the biopsy procedure. The needle preferably has an outer diameter of about 0.015 inch. In some embodiments, needle 140 is selectively extendable from and retractable into the catheter shaft.

In another embodiment, the biopsy jaws are electrically insulated from each other by forming pivot bearing 34 from electrically insulating material (e.g., DELRIN™) and by inserting electrically insulating material the exposed surfaces of the jaws. In operation, the jaws are opened and are positioned about a tissue sample. The biopsy jaws are then closed and a voltage is applied to the electrode surfaces of the jaws, creating an arc therebetween for cutting the tissue. The jaws are then completely closed to retain the cut sample within the cavity defined by the jaws.

Referring to FIGS. 7 and 7A, in another embodiment, deflectable biopsy catheter 150 includes two jaws 152, 154 designed for sampling cardiac tissue and for ablating arrhythmic tissue. Jaws 152, 154 respectively include hollow cup sections 156, 158 and solid, flat ablation electrode sections 160, 162. The electrode sections are electrically insulated from the cup sections by insulating layers 164, 166 (e.g., made from teflon). Catheter 150 also includes at least one ring electrode 168 mounted on the catheter tip. An electrode lead wire 170 is coupled to the ring electrode and extends to the proximal end of the catheter to provide electrical communication with the ring electrode.

In a presently preferred embodiment, each jaw is made from stainless steel and is about 4 mm long by about 2 mm wide. When closed, the two jaws form a generally hemispherical cavity with a diameter of about 2 mm. When open, the exposed electrode surface area (corresponding to the flat surfaces of ablation electrode sections 160, 162) is about 4 $mm^2$.

Figure 8:
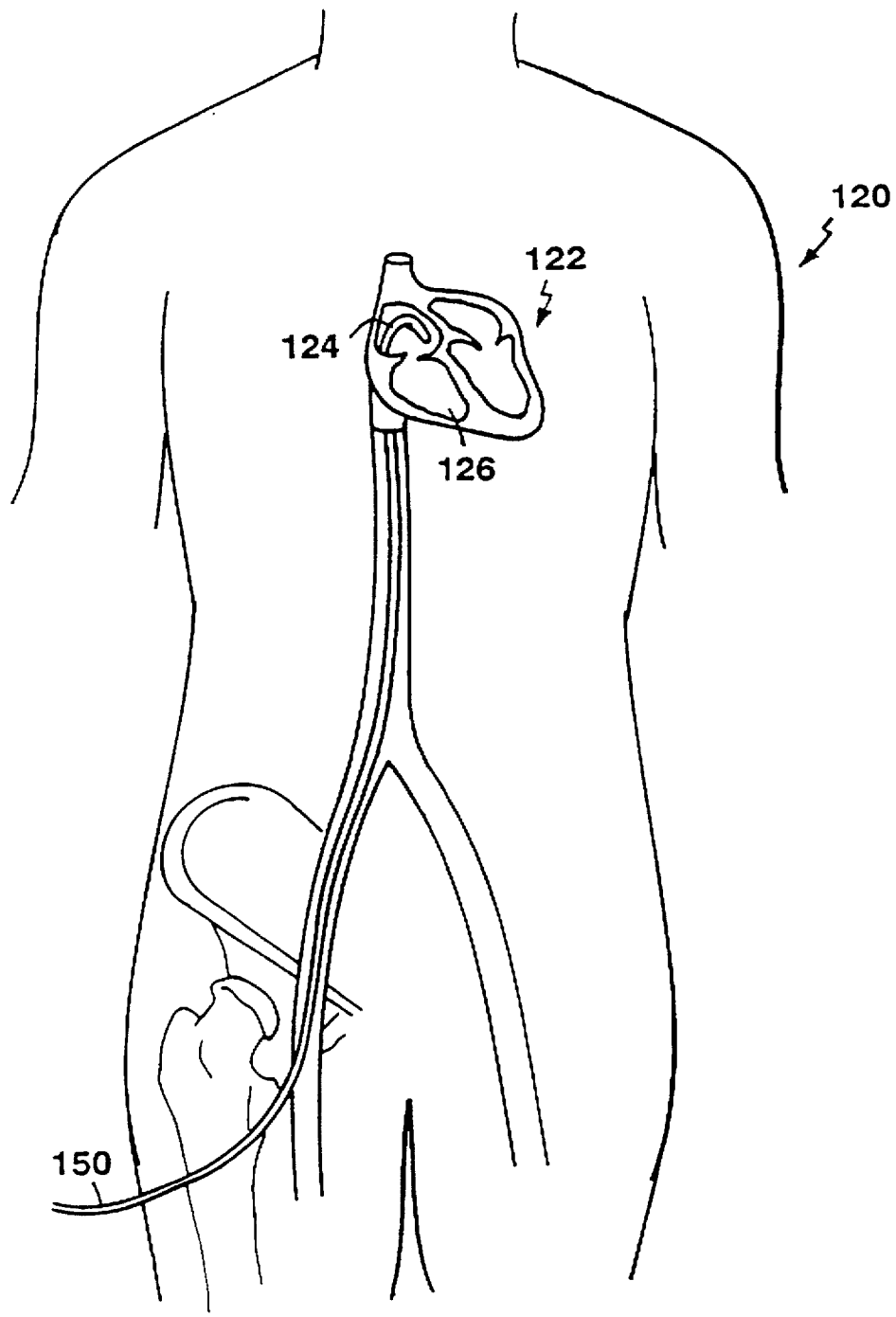
FIG. 8 is a diagrammatic view of the catheter of FIG. 7 disposed within the vasculature of a patient.

Referring to FIG. 8, in an electrophysiology procedure, deflectable biopsy ablation catheter 150 is introduced through an introducer sheath into the right femoral artery of a patient 120 by use of the Seldinger technique (alternatively, the catheter may be introduced through the left femoral artery or through the right or left femoral vein, depending upon the region of the heart to be accessed). An operator advances the catheter under fluoroscopic guidance through the patient's vasculature by simultaneously deflecting the distal tip of the catheter and applying torque to the proximal end of the catheter. The catheter is advanced through the inferior vena cava until the catheter tip 18 is positioned in a chamber of the patient's heart 122 (e.g., in the right atrium 124). The catheter enters the right atrium in an undeflected state. The operator maneuvers steerable tip 18 around the anatomical structure of the heart to position the biopsy jaws into the region of the heart that is to be mapped or ablated (e.g., the right ventricle 126). Thus, the deflectability of the catheter permits the operator to accurately position the electrodes against the desired portion of the heart wall.

Figure 8A:
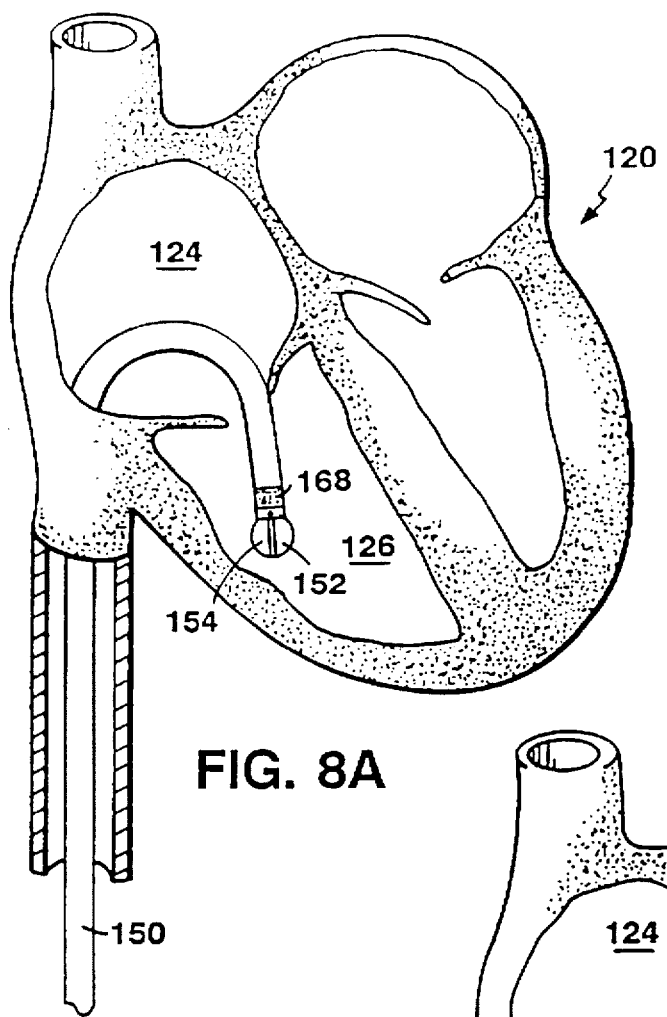
FIG. 8A is a diagrammatic side view of the distal end of the catheter of FIG. 7 measuring electrical potentials within the heart of a patient.

Referring to FIG. 8A, with jaws 152, 154 in closed position, the biopsy jaws and ring electrode 168 are used to locate the region of the heart wall that is to be sampled (and possibly ablated). Differential electrical signals from the heart wall and the blood volume within the right ventricle are detected between the ring electrode and the biopsy jaws (or between the ring electrode and one or more additional ring electrodes, if present). These signals are delivered through electrical wire 170 and actuation wire 60 to a processor and to a display device for analysis.

Figure 8B:
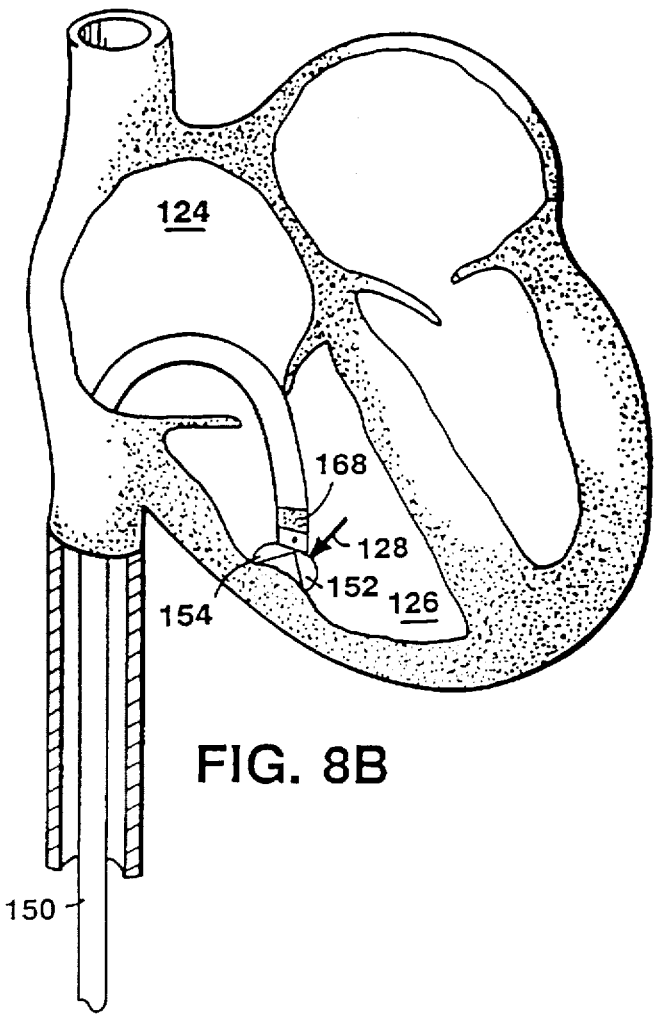
FIG. 8B is a diagrammatic side view of the distal end of the catheter of FIG. 7 positioned to take a sample within the heart of a patient.

Referring to FIG. 8B, when the location of the region of heart tissue to be sampled (ablated) is determined, the jaws are opened by moving the actuation knob distally (as indicated by arrow 64 in FIG. 1). With the jaws fully open, the catheter tip is deflected by pushing distally on thumbrest 108 (indicated by arrow 56 in FIG. 1), which presses the jaws against the myocardial tissue, increasing the normal force 128 applied by the electro-coagulation surfaces of the jaws. The deflection of the catheter tip is locked in place by twisting the piston relative to the handle housing. The operator then moves the actuation knob in the proximal direction to close the jaws about the selected portion of tissue and to cut the tissue. The cut tissue is retained within the cavity defined by the jaws during removal of the catheter from the patient's body.

If the selected region of tissue is to be ablated, the operator moves the actuation know in the proximal direction to partially close the jaws, thereby actively fixing (gripping) the catheter tip onto the tissue to be ablated. Rf energy is delivered through the actuation wire to the jaws until the desired amount of myocardial tissue is ablated (e.g., for a period of about 30 seconds to 1 minute). The combination of the fixation feature and the large surface area of the electrode sections exposed for contact with heart tissue enables deep, large area ablations to be achieved with a high degree of control.

We note the following co-pending applications, which are all herein incorporated by reference: Ser. No. 08/138,863, filed Oct. 19, 1993, U.S. Ser. No. 08/038,903, filed Mar. 29, 1993, and U.S. Ser. No. 08/086,543, filed Jul. 1, 1993, and U.S. Ser. No. 08/395,454, filed Feb. 28, 1995, to Klein et al., and entitled "Deflectable Catheter for Ablating Cardiac Tissue."

Still other embodiments are within the scope of the claims.

What is claimed is:

1. A deflectable biopsy catheter for obtaining a tissue sample from a body cavity of a patient, the catheter comprising:

an elongate catheter shaft having a body portion defining a proximal end and a distal end, a flexible tip portion associated with the distal end of the body portion, and a lumen extending from the body portion to the tip portion, the catheter shaft being sized and constructed to be advanced into a body cavity of a patient;

a deflection wire extending through the lumen and attached to the flexible tip portion of the catheter shaft; and a pair of biopsy jaws coupled to the flexible tip portion of the catheter shaft and having first and second opposed free cutting surfaces exposable for contact with a selected area of tissue within the patient's body cavity and movable with respect to each other to cut a tissue sample from the selected area of tissue.

2. A biopsy catheter as claimed in claim 1, wherein the deflection wire is attached to a surface of the lumen located within the flexible tip portion.

3. A biopsy catheter as claimed in claim 1, wherein the body portion of the catheter shaft defines a first stiffness, the flexible tip portion of the catheter shaft defines a second stiffness, and the first stiffness is greater than the second stiffness.

4. A biopsy catheter as claimed in claim 1, wherein the biopsy jaws comprise hollow substantially cup-shaped members.

5. A biopsy catheter as claimed in claim 1, wherein the biopsy jaws are pivotal hinged together about a pivot bearing coupled the flexible tip portion of the catheter shaft.

6. A biopsy catheter as claimed in claim 1, further comprising:

an elongate actuation wire coupled to the biopsy jaws and extending proximally therefrom to the proximal end of the body portion of the catheter shaft.

7. A biopsy catheter as claimed in claim 6, wherein the lumen defines a first lumen, the catheter shaft defines a second lumen that is non-coaxial with the first lumen, and the actuation wire is located within the second lumen.

8. A biopsy catheter as claimed in claim 6, further comprising:

a handle associated with the proximal end of the catheter shaft;

a piston slidably received within the handle and connected to the deflection wire such that movement of the piston relative to the handle causes deflection of the flexible tip portion of the catheter shaft; and a manually operable element movable relative to the piston and connected to the actuation wire such that movement of the manually operable element causes the jaws to move relative to one another.

9. A biopsy catheter as claimed in claim 8, wherein the piston has a slot formed therein and the manually operable element slides within the slot.

10. A biopsy catheter as claimed in claim 9, wherein the manually operable element comprises a knob mounted on a slide bar.

11. A biopsy catheter as claimed in claim 1, wherein the opposed jaws are formed from electrically conducting material and together form a generally dome-shaped outer electrically conducting surface.

12. A biopsy catheter as claimed in claim 11, wherein the actuation wire comprises conductive material.

13. A biopsy catheter as claimed in claim 11, wherein the biopsy jaws are pivotably hinged together about a pivot bearing coupled to the flexible tip portion of the catheter shaft and the pivot bearing is formed from electrically insulating material.

14. A biopsy catheter as claimed in claim 1, wherein the respective cutting surfaces of the biopsy jaws comprise a plurality of serrated teeth for cutting body tissue.

15. A biopsy catheter as claimed in claim 1, further comprising:

a needle coupled to the flexible tip portion of the catheter shaft and adapted to penetrate body tissue to a preselected depth.

16. A biopsy catheter as claimed in claim 1, wherein the biopsy jaws respectively include hollow substantially cup-shaped distal sections and proximally located ablation electrode sections, the ablation electrode sections being electrically insulated from the substantially cup-shaped distal sections.

17. A biopsy catheter as claimed in claim 16, wherein the ablation electrode sections are substantially flat.

18. A biopsy system for obtaining a tissue sample from a body cavity of a patient comprising:

a tubular member defining a longitudinally extending channel having a distal end and a proximal end; and a deflectable biopsy catheter adapted to pass through the distal end of the longitudinally extending channel of the tubular member and bend relative to the distal end of the longitudinally extending channel, the deflectable biopsy catheter including an elongate catheter shaft having a body portion defining a proximal end and a distal end, a flexible tip portion associated with the distal end of the body portion, and a lumen extending from the body portion to the tip portion, the catheter shaft being sized and constructed to be advanced into a body cavity of a patient, a deflection wire extending through the lumen and attached to the flexible tip portion of the catheter shaft, and a pair of biopsy jaws coupled to the flexible tip portion of the catheter shaft and having first and second opposed free cutting surfaces exposable for contact with a selected area of tissue within the patient's body cavity and movable with respect to each other to cut a tissue sample from the selected area of tissue.

19. A biopsy sysytem as claimed in claim 18, wherein the tubular member comprises an endoscope.

20. A biopsy sysytem as claimed in claim 18, wherein the tubular member comprises a sheath.

21. A biopsy system as claimed in claim 18, wherein the deflection wire is attached to a surface of the lumen located within the fexible tip portion.

22. A biopsy system as claimed in claim 18, wherein the body portion of the catheter shaft defines a first stiffness, the flexible tip portion of the catheter shaft defines a second stiffness, and the first stiffness is greater than the second stiffness.

23. A biopsy system as claimed in claim 18, wherein the biopsy jaws comprise hollow substantially cup-shaped members.

24. A biopsy system as claimed in claim 18, wherein the biopsy jaws are pivotal hinged together about a pivot bearing coupled to the flexible tip portion of the catheter shaft.

25. A biopsy system as claimed in claim 18, further comprising:

an elongate actuation wire coupled to the biopsy jaws and extending proximally therefrom to the proximal end of the body portion of the catheter shaft.

26. A biopsy system as claimed in claim 25, wherein the lumen defines a first lumen, the catheter shaft defines a second lumen that is non-coaxial with the first lumen, and the actuation wire is located within the second lumen.

27. A biopsy system as claimed in claim 25, further comprising:

a handle associated with the proximal end of the catheter shaft;

a piston slidably received within the handle and connected to the deflection wire such that movement of the piston relative to the handle causes deflection of the flexible tip portion of the catheter shaft; and a manually operable element movable relative to the piston and connected to the actuation wire such that movement of the manually operable element causes the jaws to move relative to one another.

28. A biopsy system as claimed in claim 27, wherein the piston has a slot formed therein and the manually operable element slides within the slot.

29. A biopsy system as claimed in claim 28, wherein the manually operable element comprises a knob mounted on a slide bar.

30. A biopsy system as claimed in claim 18, wherein the opposed jaws are formed from electrically conducting material and together form a generally dome-shaped outer electrically conducting surface.

31. A biopsy system as claimed in claim 30, wherein the actuation wire comprises conductive material.

32. A biopsy system as claimed in claim 30, wherein the biopsy jaws are pivotably hinged together about a pivot bearing coupled to the flexible tip portion of the catheter shaft and the pivot bearing is formed from electrically insulating material.

33. A biopsy system as claimed in claim 18, wherein the respective cutting surfaces of the biopsy jaws comprise a plurality of serrated teeth for cutting body tissue.

34. A biopsy system as claimed in claim 18, further comprising:

a needle coupled to the flexible portion of the catheter shaft and adapted to penetrate body tissue to a preselected depth.

35. A biopsy system as claimed in claim 18, wherein the biopsy jaws respectively include hollow substantially cup-shaped distal sections and proximally located ablation electrode sections, the ablation electrode sections being electrically insulated from the substantially cup-shaped distal sections.

36. A biopsy system as claimed in claim 35, wherein the ablation electrode sections are substantially flat.

37. A method of obtaining a tissue sample from a body cavity of a patient, comprising the steps of:

advancing a biopsy system, as defined in claim 18, within the body cavity of the patient;

advancing at least the flexible tip portion of the catheter shaft beyond the distal end of the longitudinally extending channel in the tubular member;

bending the flexible tip portion of the catheter shaft relative to the distal end of the longitudinally extending channel to steer the flexible tip portion to a preselected portion of body tissue within the body cavity by selectively applying tension to the deflection wire;

opening the opposed jaws in the vicinity of the selected portion of body tissue; and closing the jaws to cut a sample of tissue from the selected portion of body tissue.

38. A method as claimed in claim 37, wherein the opposed biopsy jaws together form an exposed electrically conductive surface, the method further comprising the step of:

electro-coagulating the selected area of tissue by supplying to the electrically conductive surface formed by the biopsy jaws energy sufficient to achieve tissue electro-coagulation.

39. A method as claimed in claim 38 further comprising the step of:

deflecting the flexible tip portion of the catheter to increase pressure applied by the exposed conductive surface of the biopsy jaws against the selected portion of tissue during electro-coagulation.

40. A method of obtaining a tissue sample from the heart of a patient, comprising the steps of:

advancing a biopsy system, as defined in claim 18, through the vasculature of a patient, wherein the opposed biopsy jaws together form a first exposed electrically conductive electrode surface and the catheter shaft includes second electrically conductive electrode surface;

steering the system through the vasculature and into the heart of the patient;

advancing at least the flexible tip portion of the catheter shaft beyond the distal end of the longitudinally extending channel in the tubular member;

bending the flexible tip portion of the catheter shaft relative to the distal end of the longitudinally extending channel to steer the flexible tip portion to preselected portions of tissue within the heart by selectively applying tension to the deflection wire;

selecting the area of heart tissue to be diagnosed based on measurements of electrical potentials within the patient's heart between the first and second electrode surfaces;

opening the opposed jaws in the vicinity a selected portion of heart tissue;

and closing the jaws to cut a sample of tissue from the selected portion of heart tissue.

41. A method as claimed in claim 40, further comprising the steps of:

selecting an area of heart tissue to be ablated based on measurements of electrical potentials within the heart between the first and second electrode surfaces, and ablating the area of heart tissue selected to be ablated by supplying to the electrically conductive surface formed by the biopsy jaws energy sufficient to achieve tissue ablation.

* * * * *